(12) United States Patent
Makihira

(10) Patent No.: US 9,408,532 B2
(45) Date of Patent: Aug. 9, 2016

(54) IMAGE PROCESSING APPARATUS AND IMAGE PROCESSING METHOD

(71) Applicant: CANON KABUSHIKI KAISHA, Tokyo (JP)

(72) Inventor: Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 36 days.

(21) Appl. No.: 13/780,094

(22) Filed: Feb. 28, 2013

(65) Prior Publication Data

US 2013/0235342 A1 Sep. 12, 2013

(30) Foreign Application Priority Data

Mar. 8, 2012 (JP) ................................ 2012-051449

(51) Int. Cl.
*A61B 3/00* (2006.01)
*A61B 3/14* (2006.01)
(Continued)

(52) U.S. Cl.
CPC .............. *A61B 3/0058* (2013.01); *A61B 3/0041* (2013.01); *A61B 3/10* (2013.01);
(Continued)

(58) Field of Classification Search
CPC ........ A61B 3/14; A61B 3/102; A61B 3/0066; A61B 3/1233; A61B 3/113; A61B 3/12; A61B 3/152; A61B 5/0066; G06T 2207/30041; G06T 2207/10101; G06T 7/0012; G06T 7/0024; G06T 7/0026; G06T 7/0028; G06T 7/003; G06T 7/0034; G06T 7/0036; G06T 7/0038; G06K 2209/05; G01B 9/02044; G01B 9/02068; G01B 9/02091

USPC .......... 351/219, 221, 246, 206, 208; 356/479; 382/128, 130, 131, 173; 600/407, 425; 359/450, 497; 348/78
See application file for complete search history.

(56) References Cited

U.S. PATENT DOCUMENTS 6,810,140 B2 * 10/2004 Yang et al. .................... 382/154
7,570,791 B2 * 8/2009 Frank et al. ................... 382/132
(Continued)

FOREIGN PATENT DOCUMENTS

JP     2008-237238 A     10/2008
JP     2011-254959 A     12/2011

OTHER PUBLICATIONS

Kim L. Boyer, Artemas Herzog, and Cynthia Roberts. Automatic Recovery of the Optic Nervehead Geometry in Optical Coherence Tomography. IEEE Transactions on Medical Imaging, vol. 25, No. 5, May 2006.*

(Continued)

*Primary Examiner* — Bumsuk Won
*Assistant Examiner* — Collin X Beatty
(74) *Attorney, Agent, or Firm* — Fitzpatrick, Cella, Harper & Scinto

(57) ABSTRACT

In an image processing apparatus that irradiates an object to be inspected with measuring light and synthesizing a plurality of tomographic images acquired on the basis of reflected light to form a new tomographic image in order to reduce speckles in the image and enhance the image quality of the resultant composed image in imaging using optical coherence tomography, the image processing apparatus is provided with an image acquiring unit that acquires a plurality of tomographic images of an object to be inspected and a selection unit that selects tomographic images to be composed from among the plurality of tomographic images on the basis of similarity information about the plurality of tomographic images.

30 Claims, 8 Drawing Sheets

(51) Int. Cl.
*A61B 3/10* (2006.01)
*G06T 7/00* (2006.01)

(52) U.S. Cl.
CPC ............. *A61B 3/14* (2013.01); *G06K 2209/05* (2013.01); *G06T 7/0012* (2013.01); *G06T 7/0024* (2013.01); *G06T 2207/10101* (2013.01); *G06T 2207/30041* (2013.01)

(56) References Cited

U.S. PATENT DOCUMENTS

| | | | |
|---|---|---|---|
| 7,831,075 B2* | 11/2010 | Wilson et al. | 382/128 |
| 7,995,810 B2* | 8/2011 | Li et al. | 382/128 |
| 8,348,426 B2 | 1/2013 | Tsukada et al. | |
| 8,983,164 B2 | 3/2015 | Iwase et al. | |
| 9,171,367 B2 | 10/2015 | Iwase et al. | |
| 2006/0159319 A1* | 7/2006 | Sathyanarayana | 382/128 |
| 2006/0164653 A1* | 7/2006 | Everett | A61B 3/102 356/479 |
| 2006/0227333 A1* | 10/2006 | Tearney | A61B 5/0059 356/512 |
| 2006/0228011 A1* | 10/2006 | Everett et al. | 382/128 |
| 2007/0258630 A1* | 11/2007 | Tobin et al. | 382/128 |
| 2008/0100612 A1* | 5/2008 | Dastmalchi et al. | 345/418 |
| 2008/0234972 A1 | 9/2008 | Tsukada et al. | |
| 2008/0240527 A1* | 10/2008 | Keller | G06F 17/30259 382/128 |
| 2008/0309881 A1* | 12/2008 | Huang et al. | 351/246 |
| 2009/0005691 A1* | 1/2009 | Huang et al. | 600/476 |
| 2009/0028400 A1* | 1/2009 | Ishikawa et al. | 382/128 |
| 2009/0268162 A1* | 10/2009 | Stetson et al. | 351/246 |
| 2010/0166280 A1* | 7/2010 | Endo et al. | 382/131 |
| 2010/0172556 A1* | 7/2010 | Cohen et al. | 382/128 |
| 2010/0278402 A1* | 11/2010 | Everett et al. | 382/128 |
| 2011/0034803 A1* | 2/2011 | Stetson | 600/425 |
| 2011/0063573 A1* | 3/2011 | Meyer et al. | 351/246 |
| 2011/0137157 A1* | 6/2011 | Imamura | G06T 7/0012 600/425 |
| 2011/0150310 A1* | 6/2011 | Endo et al. | 382/131 |
| 2011/0211057 A1* | 9/2011 | Iwase et al. | 348/78 |
| 2011/0234978 A1* | 9/2011 | Hammer | A61B 3/102 351/208 |
| 2011/0242306 A1* | 10/2011 | Bressler et al. | 348/78 |
| 2011/0243415 A1* | 10/2011 | Yonezawa et al. | 382/131 |
| 2011/0267340 A1* | 11/2011 | Kraus et al. | 345/419 |
| 2011/0275931 A1* | 11/2011 | Debuc | 600/425 |
| 2011/0282181 A1* | 11/2011 | Wang et al. | 600/407 |
| 2012/0002166 A1 | 1/2012 | Tomatsu et al. | |
| 2012/0026310 A1* | 2/2012 | Mizukusa et al. | 348/78 |
| 2012/0154747 A1 | 6/2012 | Makihira | |
| 2012/0218516 A1* | 8/2012 | Imamura | A61B 3/1241 351/206 |
| 2012/0229761 A1 | 9/2012 | Makihira | |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2012/0327365 A1 | 12/2012 | Makihira | |
| 2013/0070988 A1 | 3/2013 | Makihira | |
| 2013/0216115 A1* | 8/2013 | Iwase | G06T 7/0026 382/131 |
| 2015/0110378 A1 | 4/2015 | Iwase et al. | |
| 2016/0000321 A1 | 1/2016 | Iwase et al. | |

OTHER PUBLICATIONS

Adolf F. Fercher. Optical Coherence Tomography. Journal of Biomedical Optics 1(2), 157-173 (Apr. 1996).*

Amardeep S. G. Singh, Tilman Schmoll, and Rainer A. Leitgeb. Segmentation of Doppler optical coherence tomography signatures using a support-vector machine. Biomed Opt Express. May 1, 2011; 2(5): 1328-1339. Published online Apr. 26, 2011. doi: 10.1364/BOE.2.001328.*

* cited by examiner

IMAGE PROCESSING APPARATUS AND IMAGE PROCESSING METHOD

BACKGROUND OF THE INVENTION

1. Field of the Invention

The present invention relates to an image processing apparatus and image processing method for performing image processing of a tomographic image acquired by an optical coherence tomography imaging apparatus.

2. Description of the Related Art

In recent years, optical coherence tomography imaging apparatuses utilizing the principle of optical coherence tomography (which will be hereinafter abbreviated as OCT) have been put to practical use. In the optical coherence tomography, measuring light is made incident on a predetermined portion of an object to be inspected, and the structure of the object in the depth direction at the position at which the measuring light is incident is imaged on the basis of interference light of the reflected or diffused measuring light and reference light from a reference object. With this apparatus, light is made incident on the fundus to scan the retina, thereby acquiring a two-dimensional or three-dimensional tomographic image of the fundus. This enables the observation of the fundus.

In order to improve the image quality (specifically, the S/N ratio) of a tomographic image acquired by the OCT, there has been developed a known technique in which a plurality of images are averaged to generate a high-quality tomographic image. Japanese Patent Application Laid-Open No. 2008-237238 discloses a technique of generating a high-quality still image by creating a new tomographic image by computation on the basis of a tomographic image in a cross section adjoining to the cross section of a tomographic image of a retina capture beforehand.

In the prior art described in Patent Application Laid-Open No. 2008-237238, the scanning position with respect to the sub-scanning direction is varied. Therefore, if the eyeball moves in the sub-scanning direction, it is possible that a tomographic image cannot be captured at a desired position and that a high-quality composed image cannot be formed.

Moreover, in this prior art, since consecutive images are selected from among tomographic images captured during scanning to form a still image, the number of images to be composed to form a new image is generally fixed. Therefore, there is a limit to the image quality.

SUMMARY OF THE INVENTION

An object of the present invention is to achieve a further enhancement of the image quality by appropriately selecting the number of tomographic images to be composed.

Another object of the present invention is to reduce speckle noises, which are made visible by synthesizing of tomographic images, thereby achieving a further enhancement of the image quality.

To achieve the above object, the image processing apparatus according to the present invention comprises: an image acquiring unit that acquires a plurality of tomographic images of an object to be inspected; and a selection unit that selects tomographic images to be composed from among the plurality of tomographic images on the basis of similarity information about the plurality of tomographic images.

To achieve the above object, the image processing method according to the present invention comprises the steps of:

acquiring a plurality of tomographic images of an object to be inspected; and selecting tomographic images to be composed from among the plurality of tomographic images on the basis of similarity information about the plurality of tomographic images.

According to the present invention, an image having enhanced image quality can be formed by setting the number of images to be composed.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

In the first embodiment, there will be described an exemplary case in which a high-quality composed tomographic image is formed by using an OCT apparatus as an apparatus for acquiring tomographic images of an object to be inspected (such as an eye to be inspected or the skin of an object to be inspected) to acquire a plurality of tomographic images of the fundus, measuring similarity information (information concerning the similarity) of the plurality of tomographic images, and determining the number of tomographic images to be added (to be composed) on the basis of the similarity information.

Figure 1:
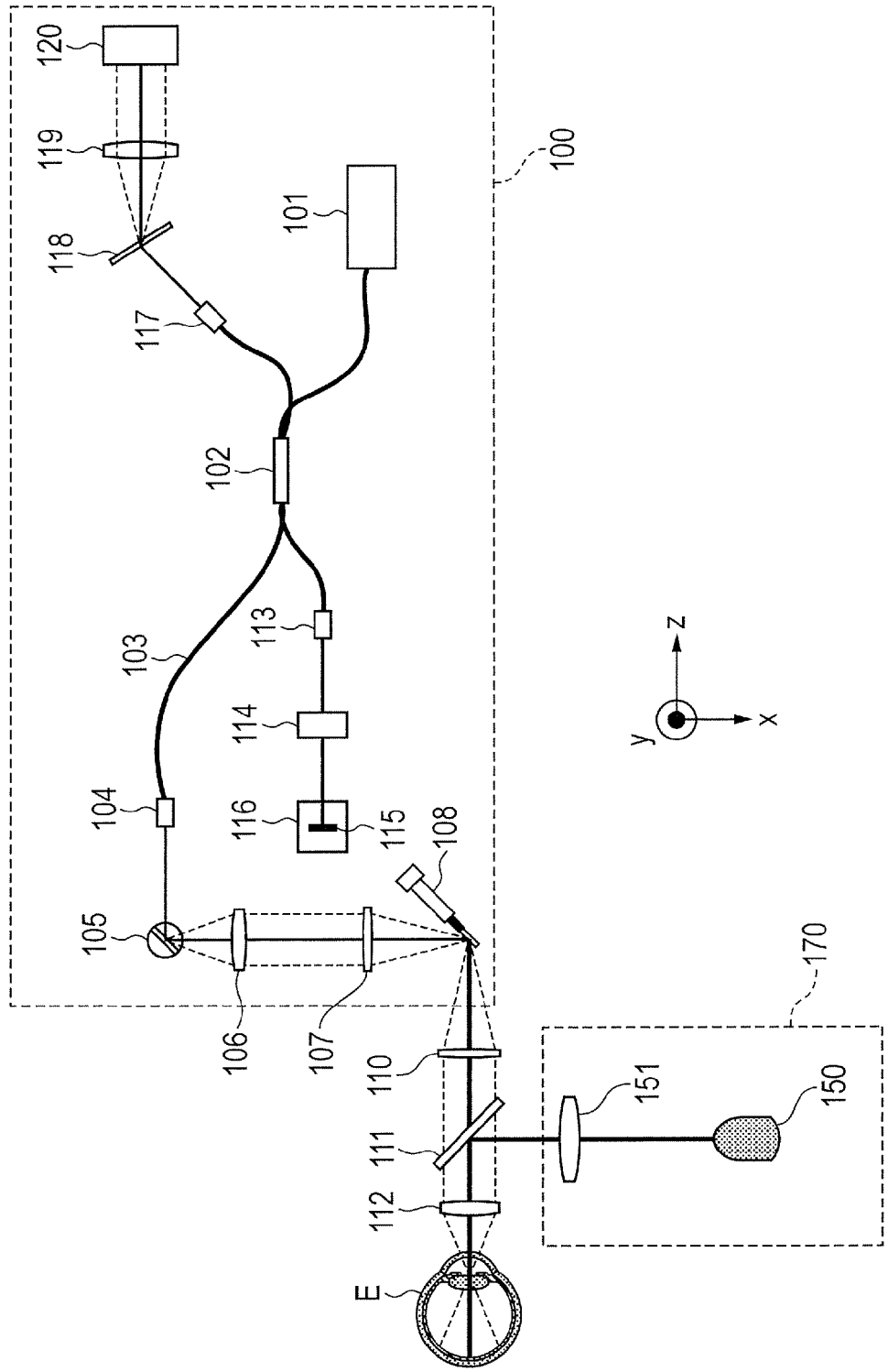
FIG. 1 is a schematic diagram showing the configuration of an optical unit used in a first embodiment.

An optical unit used in this embodiment will be described with reference to FIG. 1. The optical unit includes an OCT apparatus 100 and a fixation target device 170.

The OCT apparatus has a light source 101, which is an SLD (Super Luminescent Diode) light source having a center wavelength of 840 nm and a full width at half maximum wavelength of 45 nm. Instead of the SLD light source, an ASE (Amplified Spontaneous Emission) light source may also be suitably used. Wavelengths near 850 nm and near 1050 nm are suitable for imaging of the fundus. Low-coherence light emitted from the light source 101 passes through a fiber to enter a fiber coupler 102, where light is split into measuring light (which is also referred to as OCT beam) and reference light.

While an interferometric system arrangement using fibers is described, an arrangement using a beam splitter in a spatial optical system may be adopted alternatively.

The measuring light passes through a fiber 103 and is emitted from a fiber collimator 104 as parallel light. The measuring light further passes through an OCT scanner (Y) 105, relay lenses 106, 107, an OCT scanner (X) 108, a scan lens 110, a dichroic mirror 111, and an eyepiece lens 112 to enter an eye to be inspected E. The beam diameter of the measuring light at the fundus is approximately 20 µm. Galvano scanners are used as the OCT scanner (X) 108 and the OCT scanner (Y) 105. The measuring light incident on the eye to be inspected E is reflected by the retina and returns to the fiber coupler 102 through the same optical path.

On the other hand, the reference light is guided from the fiber coupler 102 to a fiber collimator 113 and is emitted from it as parallel light. The emitted reference light passes through a dispersion correction glass 114 and is reflected by a reference mirror 115 on an optical path varying stage 116. The reference light reflected by the reference mirror 115 returns to the fiber coupler 102 through the same optical path. The returning measuring light and reference light are combined in the fiber coupler 102 and guided to a fiber collimator 117. In this specification, the combined light is referred to as interference light.

The fiber collimator 117, a grating 118, a lens 119, and a line sensor 120 constitute a spectroscope. The spectroscope measures the interference light to provide information about light intensities at different wavelengths (or information about light intensity as a function of wavelength). The information about light intensities at different wavelengths acquired by the line sensor 120 is transferred to a personal computer (not shown), which creates a tomographic image of the retina of the inspected eye E on the basis of this information. Hereinafter, the term "tomographic image" will refer to a tomographic image of a retina, unless stated particularly.

The fixation target device 170 used in this embodiment is an internal fixation lamp type. The fixation target 170 will be described with reference to FIG. 1, which also illustrates the OCT apparatus. The fixation target 170 has a light source 150, which is a light emitting diode (LED). The position at which light is emitted from the light emitting diode is changed under control of a personal computer (not shown) in accordance with the portion to be imaged. The light emitting diode 150 emits light having a wavelength of 500 nm. A beam emitted from the light source 150 passes through a lens 151 and the dichroic mirror 111 and is delivered to the eye to be inspected E. The dichroic mirror 111 is arranged between the scan lens 110 and the eyepiece lens 112 to split light, in terms of wavelength, into short-wavelength light (having wavelengths of about 500 nm) and an OCT beam (having wavelengths longer than 700 nm).

Figure 2:
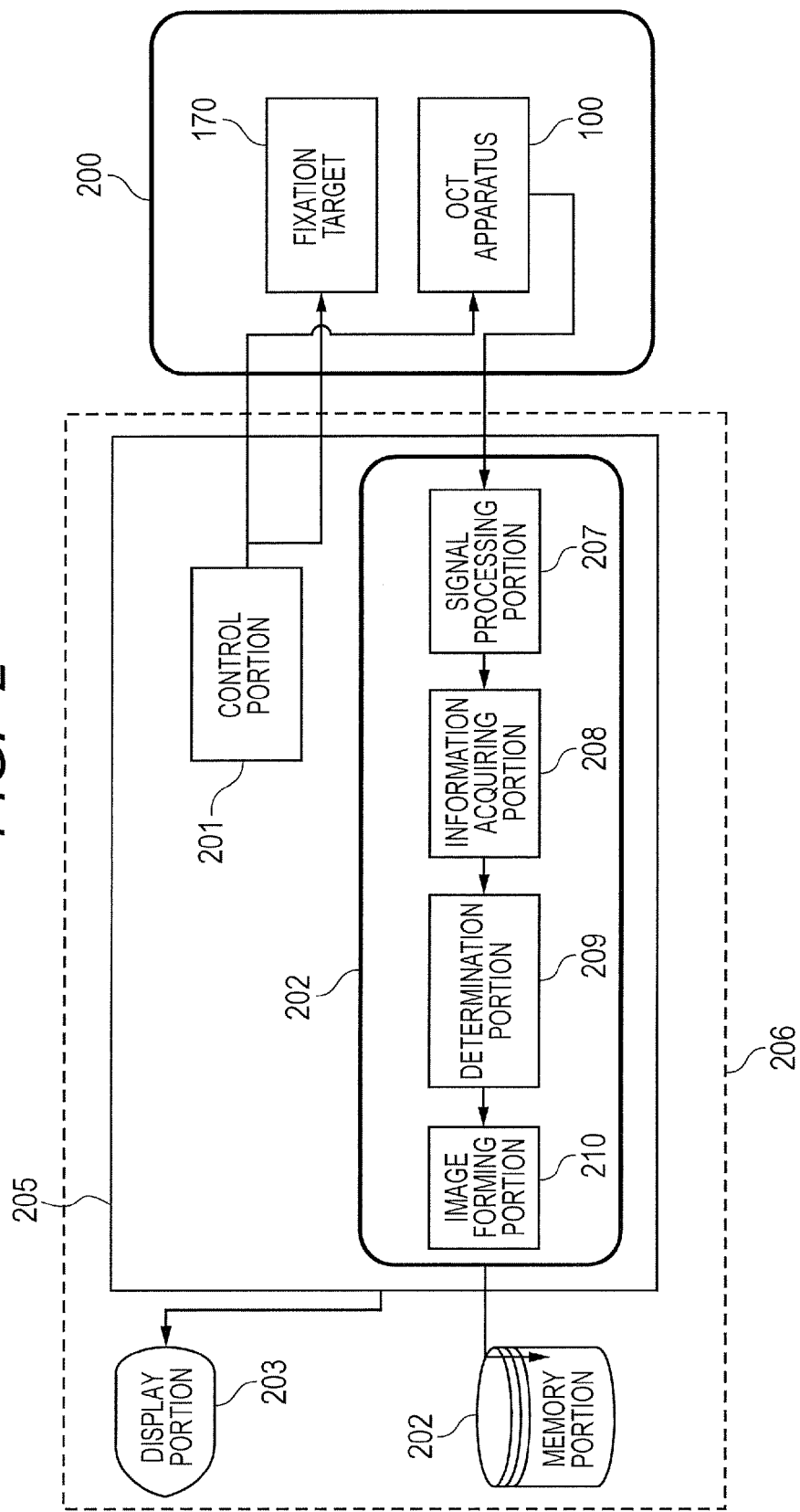
FIG. 2 is a schematic diagram showing the configuration of an image processing apparatus used in the first embodiment.

The overall construction of the system will be described with reference to FIG. 2. The system includes a control portion 201 that controls the components of the optical unit 200, an image processing unit 202 that performs image processing, an image display portion 203 that serves as an display unit displaying images, and a memory portion 204 that stores various data. The personal computer 206 has a CPU 205, the display portion 203, and the memory portion 204. The control portion 201 and the image processing unit 202 are implemented in the CPU 205.

The image processing unit 202 receives electric signals from the line sensor 120 of the OCT apparatus 100. The image processing unit 202 includes a signal processing portion 207 performing signal processing on the electric signals, an information acquiring portion (similarity information acquiring unit) 208 that acquires information concerning the similarity of images acquired by the signal processing portion 207, a determination portion (determination unit or setting unit that sets the number of images to be composed) 209 that determines the number of tomographic images to be composed on the basis of the information concerning the similarity, and a tomographic image forming portion (forming unit) 210 that composes an image on the basis of information from the determination portion. The composed tomographic image thus formed is displayed by the display portion (display unit) 203, and the data is stored in the memory portion 204. At the time of the determination of the number of images to be composed, the selection of tomographic images to be used in synthesizing an image from among the images acquired by an image acquiring unit (a unit constituted by the line sensor 120 and other components) that acquires tomographic images is also performed. Therefore, the above-described determination unit also functions as a selection unit that selects tomographic images to be used in synthesizing an image. In this selection, images are selected on the basis of the aforementioned similarity information. A plurality of tomographic images of the retina is captured using the above-described OCT apparatus.

The control portion 201 of the CPU 205 causes the OCT scanner (X) 108 to operate. In order to form a high-quality image by capturing a plurality of tomographic images of the same portion of the fundus and averaging them, the same portion of the fundus is scanned without driving the OCT scanner (Y) 105. An electric signals obtained by the line sensor 120 during the scanning is Fourier-transformed with respect to the wave number in the signal processing portion 207 to provide a tomographic image.

Figure 3A:
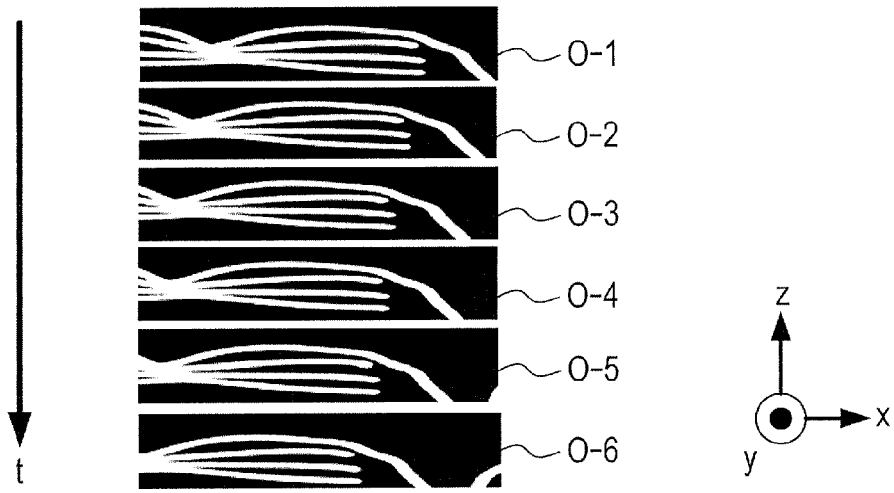
FIG. 3A illustrates a plurality of tomographic images acquired in the first embodiment arranged in order.

The scanning rate in this embodiment is 35 kA scan/sec, and an area on the fundus of a width of approximately 8 mm is scanned. Exemplary tomographic images thus obtained are shown in FIG. 3A. In this embodiment, one hundred tomographic images are acquired. Although the apparatus is controlled to scan the same portion, the tomographic images O-1 to O-6 vary with time t as shown in FIG. 3A due to movement of the eyeball.

Although the eyeball unconsciously moves (involuntary eye movement), the movement of the eyeball is limited, because it is gazing at the fixation target 150. Because the acquired tomographic images are images extending in the direction of the eye axis (Z axis direction) and the horizontal direction (X axis direction) of the plane of the fundus, different tomographic images can be composed with a positional accuracy of a few to one pixel or less by performing alignment on the basis of the images (on the basis of a characteristic point or correlation function) with respect to the X axis direction and the Z axis direction.

Movement in the direction perpendicular to the image of the fundus (Y axis direction) will cause a change in the OCT scanning position. This leads to small differences among the images as will be seen in FIG. 3A. Actually, a difference in the scanning position with respect to the Y axis direction leads to a difference in the curvature of the macula retinae (or optic papilla) in the tomographic images.

Then, the degree of similarity of tomographic images is measured. After alignment with respect to the X and Z direction has been done, the degree of similarity of the images is calculated in a common X-Z region. The degree of similarity of the images calculated here may be any value that represents the similarity of a plurality of tomographic images. In this embodiment, a cross-correlation coefficient calculated from two tomographic images is used. Specifically, the CPU 205 selects the first tomographic image among the one hundred tomographic images as a reference image, and ninety-nine cross-correlation coefficients are calculated from the reference image and the other tomographic images. Then, their ratio is used as the degree of similarity.

Figure 3B:
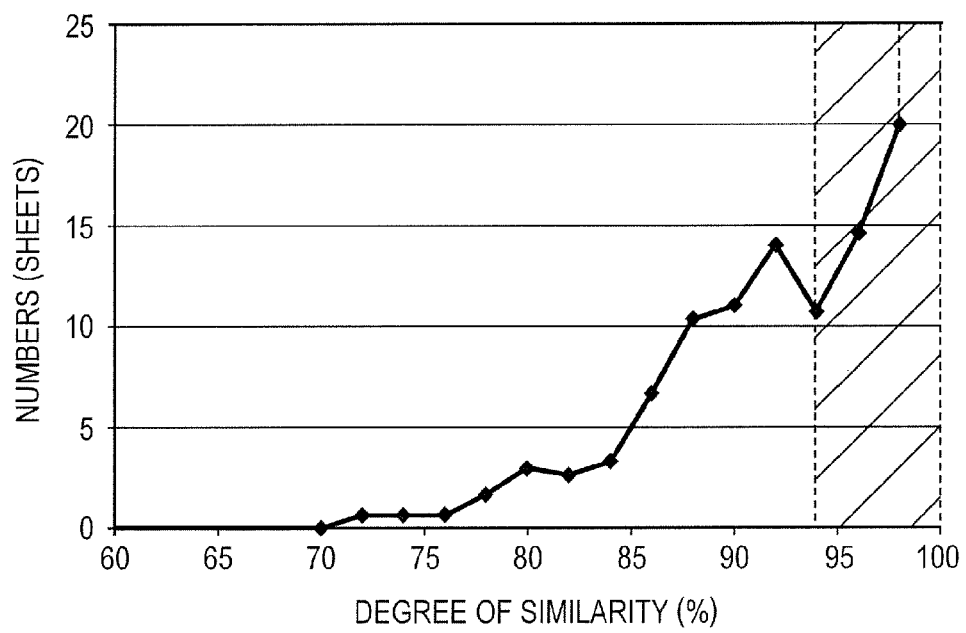
FIG. 3B is a graph showing the degree of similarity of the set of tomographic images shown in FIG. 3A.

FIG. 3B is a graph showing the degree of similarity calculated in this way and the numbers of tomographic images that have the respective degrees of similarity. As will be seen from FIG. 3B, most of the consecutively captured tomographic images have a degree of similarity not lower than 70%. In the present invention, the degree of similarity is not limited to the cross-correlation coefficient, but other method of representing the degree of similarity of images, e.g., the sequential similarity detection algorithm, may be adopted.

Now, a description will be made of the selection and the number of tomographic images to be used in the image synthesizing. If a composed image is formed only from images having high degree of similarity, speckles (signals or images not existing in the retina layer) will become conspicuous in the composed image. Because the same portion is scanned using the same optical path, the same speckle images will appear in the tomographic images. Synthesizing an image from such images will increase the S/N ratio of the speckle images as well as the image of the retina layer, making the speckles more conspicuous.

In this embodiment, to improve the S/N ratio of the image and to remove speckles, not only images having high similarity but also images having somewhat low similarity are used in synthesizing an image. Here, somewhat low similarity refers to a degree of similarity that is not so low as to make the composed image blurred. In the case of the normal eye, a misalignment of about 2.5 or less times the diameter of the measurement light beam (that is, misalignment of about 50 μm or less) will not lead to image blur. In the method of calculating the degree of similarity in this embodiment, it has been found that the diagnostic imaging is not significantly affected is images having similarity of about 94% or higher are used. In the following, an exemplary case will be specifically described with the above in mind.

In this embodiment, thirty images are composed. Tomographic images acquired in this embodiment include, as shown in FIG. 3B, twenty images having a degree of similarity in the range not lower than 98%, fourteen images having a degree of similarity in the range of lower than 98% and not lower than 96%, and eleven images having a degree of similarity in the range of lower than 96% and not lower than 94%. Taking into consideration the S/N and speckles, ten tomographic images are averaged in each range to form a composed image as a new tomographic image. Images having degrees of similarity represented by the hatched portion in FIG. 3B are used in the image synthesizing. Therefore, the number of tomographic images determined by the determination portion 209 varies depending on the degree of similarity. The higher the degree of similarity is, the larger the number of tomographic images used in the image synthesizing is. In other words, tomographic images having degrees of similarity falling in a predetermined range are selected by the selection unit and used in the image synthesizing. Moreover, tomographic images having different degrees of similarity in the predetermined range are selected for use in the image synthesizing.

The composed tomographic image and the determined number of images in each range of the degree of similarity may both be displayed to allow the operator to determine the number of images in each range of the degree of similarity. In cases where a local edema or a site of laser treatment is to be scanned, even an misalignment of 50 μm will lead to significant image blur. In such case, therefore, the misalignment may be limited to 30 μm or smaller. While in the above-described exemplary case a composed image is formed by averaging tomographic images in each range, a composed image may be formed by weighted averaging.

As described in the foregoing, a high-quality tomographic image can be formed by calculating the degree of similarity of acquired tomographic images, limiting the number of images having high degrees of similarity to be averaged, and synthesizing an image by averaging the limited number of images. The composed image thus formed is displayed by the aforementioned display unit. In the display process, a composed image or tomographic image forming portion may function as a display control unit that controls the display unit in regard to the mode of display and to cause it to select a suitable display form. Specifically, the display unit may be configured to display a plurality of tomographic images, for each of which similarity information associated therewith may be additionally displayed.

Second Embodiment

In the second embodiment, eye movement is detected from an image of the fundus in order to acquire similarity information of tomographic images, and a relative position of OCT scanning is detected. In the following, there will be described a system that forms a high-quality composed OCT image by averaging tomographic images on the basis of the relative position information thus detected. The OCT apparatus 100, the fixation target device 170, and other components in the second embodiment that are the same as those in the first embodiment will not be described further.

Figure 4:
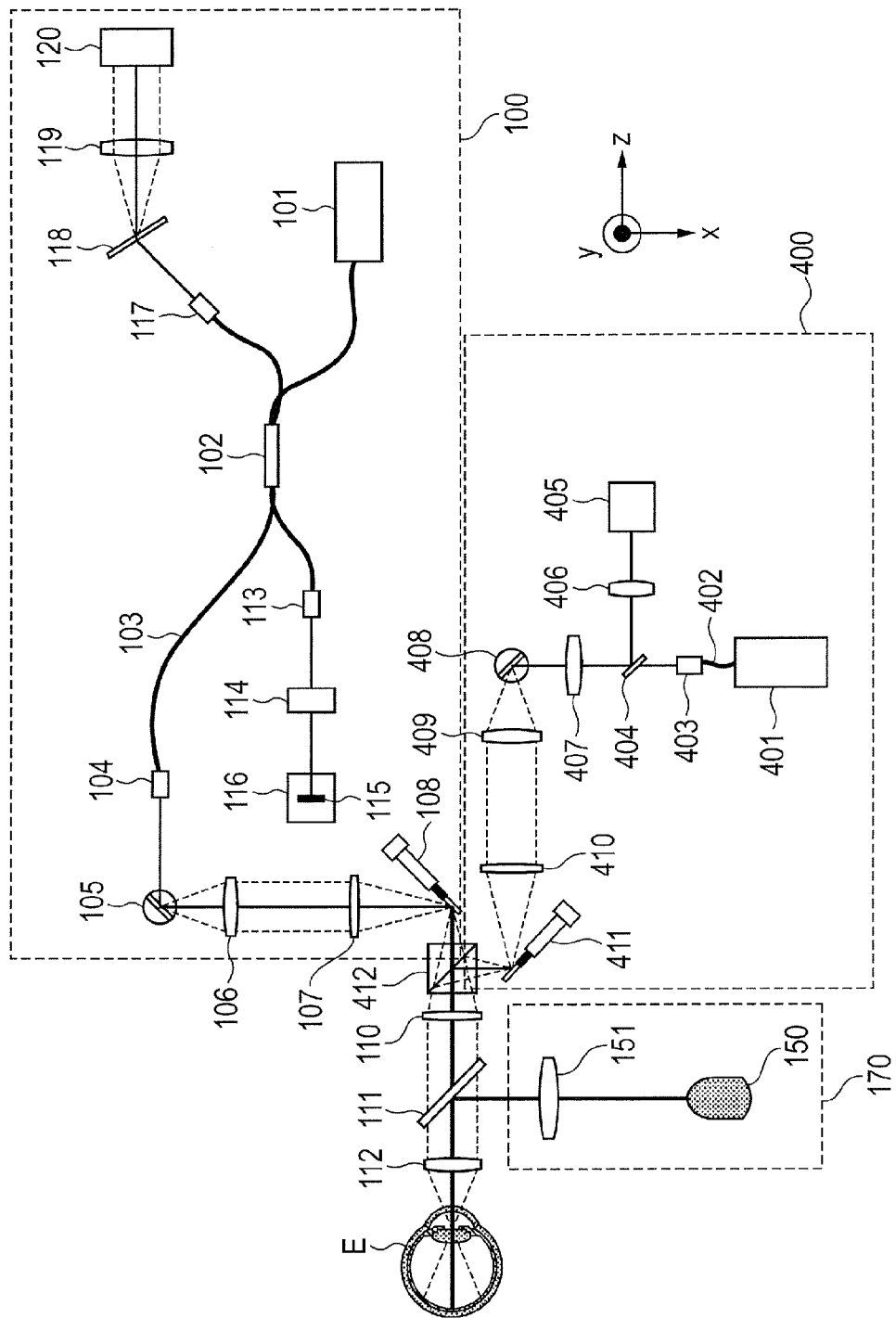
FIG. 4 is a schematic diagram showing the configuration of an optical unit used in a second embodiment.

The optical configuration of an SLO apparatus 400 that captures a fundus image will be described with reference to FIG. 4. The SLO apparatus 400 has a laser light source 401, which may be a semiconductor laser or an SLD (Super Luminescent Diode) light source, suitably. No limitation is placed on the wavelength of the light source 401 on condition that it is so different from the wavelength of the low-coherence light source 101 of the OCT apparatus that the light from the light source 401 and the light from the low-coherence light source 101 can be separated in terms of wavelength by a dichroic beam splitter 412. In view of the image quality for observation of the fundus, light having a wavelength in a near-infrared wavelength range of 700 nm to 1000 nm is suitable.

In this embodiment, a semiconductor laser having a wavelength of 760 nm is used. A laser beam (SLO beam) emitted from the laser light source 401 passes through a fiber 402 and is emitted from a fiber collimator 403 as parallel light, which is guided to an SLO scanner (Y: scanning in the vertical direction in the plane of the fundus) 408 through a perforated or ring mirror 404 and a focus lens 407 mounted on a focus stage (not shown). Then, the beam passes through lenses 409, 410 and an SLO scanner (X: scanning in the horizontal direction in the plane of the fundus) 411, and is reflected by the dichroic beam splitter 412 to enter the eye to be inspected E. The dichroic beam splitter 412 is adapted to transmit the OCT beam and to reflect the SLO beam. A galvano scanner is used as the scanner of the SLO apparatus.

The SLO beam incident on the eye to be inspected E is delivered to the fundus of the eye to be inspected E. The beam is reflected or diffused by the fundus of the eye to be inspected E and returns to the ring mirror 404 through the same optical path. The position of the ring mirror 404 is conjugate with the position of the pupil of the eye to be inspected E, and light having passed the portion around the pupil among light generated by rearward diffusion of the beam with which the fundus is irradiated is reflected by the ring mirror 404 and then focused by a lens 406 onto an avalanche photodiode (APD) 405. A fundus image, which is an image on the X-Y plane of the fundus, is formed by a later described CPU 506 on the basis of intensity information provided by the APD 405.

Figure 5:
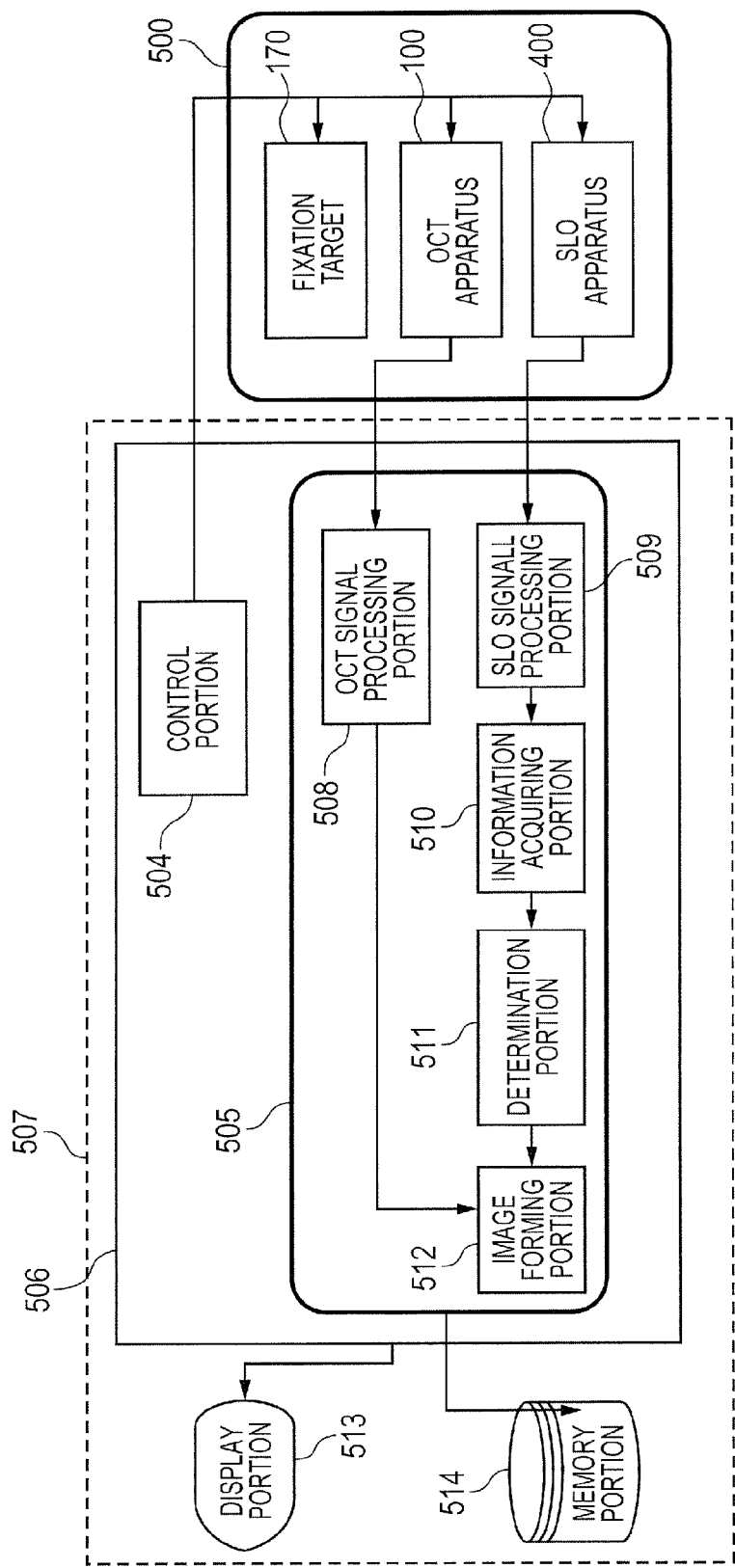
FIG. 5 is a schematic diagram showing the configuration of an image processing apparatus used in the second embodiment.

The overall construction of the apparatus or system used in this embodiment will be described with reference to FIG. 5. The apparatus includes a control portion 504 that controls the components of an optical unit 500, an image processing unit 505 that performs image processing, an image display portion 513 that displays images, and a memory portion 514 that stores various data. A personal computer 507 has the CPU 506, the display portion 513, and the memory portion 514. The image processing unit 505 has five portions including an OCT signal processing portion 508 that receives an electric signal from the line sensor 120 of the OCT apparatus 100 and performs signal processing on the electric signal, an SLO signal processing portion 509 that receives a signal representative of the fundus from the SLO apparatus 503 and processes the received signal, an information acquiring portion 510 that acquires information about movement of the fundus from the fundus image formed in the SLO signal processing portion 509, a setting or determination portion 511 that sets the number of tomographic images to be composed on the basis of the information, and a composed image forming portion 512 that composes images on the basis of information from the setting portion 511.

A plurality of tomographic images of the retina are captured using the OCT apparatus in the same manner as the first embodiment. The control portion 504 of the CPU 506 causes the OCT scanner (X) 108 to operate. In order to form a high-quality image by capturing a plurality of tomographic images of the same portion of the fundus and averaging them, the same portion of the fundus is scanned without driving the OCT scanner (Y) 105. An electric signal obtained by the line sensor 120 during the scanning is Fourier-transformed with respect to the wave number in the signal processing portion 508 to provide a tomographic image. Simultaneously, a fundus image is formed using the SLO apparatus 400. Specifically, an electric signal is received from the APD 405 of the SLO apparatus 400, and a fundus image is formed by the SLO signal processing portion 509.

In this embodiment, the OCT apparatus 100 and the SLO apparatus 400 are caused to operate simultaneously to form tomographic images and fundus images simultaneously. Imaging timing is controlled by the CPU 506, and tomographic images and fundus images are both formed at a frame rate of 30 frame/sec and stored. In this process, the CPU 506 acquires fundus images in association with tomographic images of the fundus. The CPU 506 has a module that functions as an association unit that performs this association.

Figure 6:
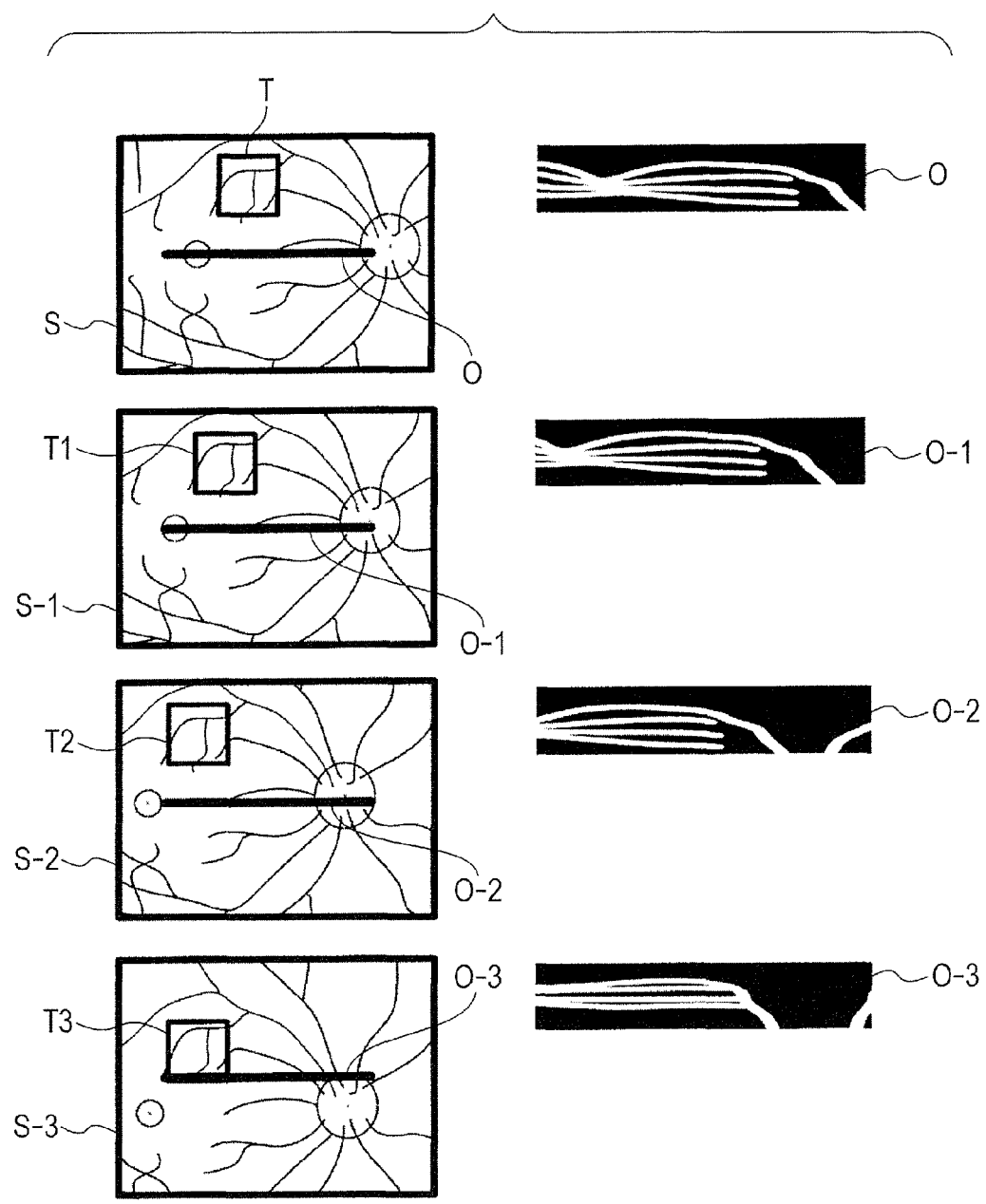
FIG. 6 schematically illustrates tomographic images and fundus images used in the second embodiment.

In the following, the process performed by the information acquiring portion 510 will be described. Captured or acquired fundus images and tomographic images are like those shown in FIG. 6. A characteristic point T (which will be hereinafter referred to as "template") such as a blood vessel is detected in the first-captured fundus image S, and a tomographic image O captured simultaneously with it is retrieved. Data such as an image of the template T and its coordinates is stored in the memory portion 507. Then, a characteristic point T1 corresponding to the characteristic point T is detected in the next-captured fundus image S-1.

By determining the coordinates of the point T1 and comparing them with the coordinates of the point T, a moving amount of the fundus image in the X-Y plane is computed as ($\Delta x$, $\Delta y$) on the coordinate system. In this embodiment, this relative position information ($\Delta x$, $\Delta y$) is used as similarity information. Data thus computed and other data including the coordinates are stored in the memory portion 514. The same processing is applied also to fundus images captured subsequently. This operation is applied to all the captured fundus image up to the i-th image S-i (i is the number of captured images). Tomographic images are captured up to the i-th image O-i.

Figure 7:
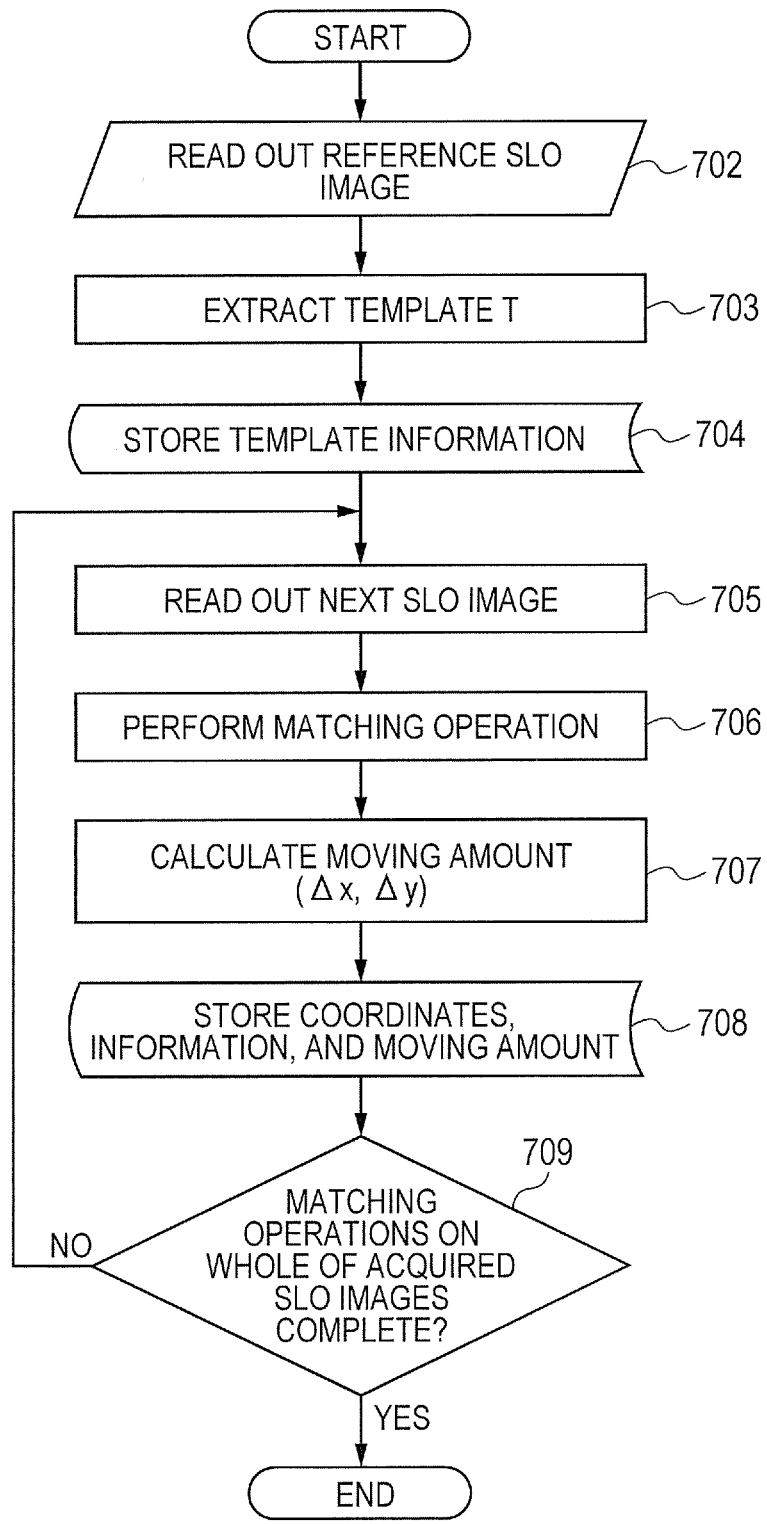
FIG. 7 is a schematic flow chart of a process performed in the second embodiment.

The above process will be specifically described with reference to a flow chart of FIG. 7. Firstly, a fundus image stored is read out from the memory portion 514 (step 702). A template T is extracted from the first fundus image thus retrieved (step 703). The image of the extracted template T and its coordinates are stored in the memory of the personal computer (step 704). Then, the next fundus image is read out (step 705). A matching operation is performed by searching for a partial image coinciding with the template T in the read-out fundus image (step 706). A moving amount ($\Delta x$, $\Delta y$) of the fundus is computed from the coordinates of the matching template T1 and the coordinates of the extracted template T (step 707). The coordinates of the matching template T1, information and the moving amount are saved (step 708). Steps 705 to 708 are executed repeatedly in the same manner for the other captured fundus images.

Figure 8:
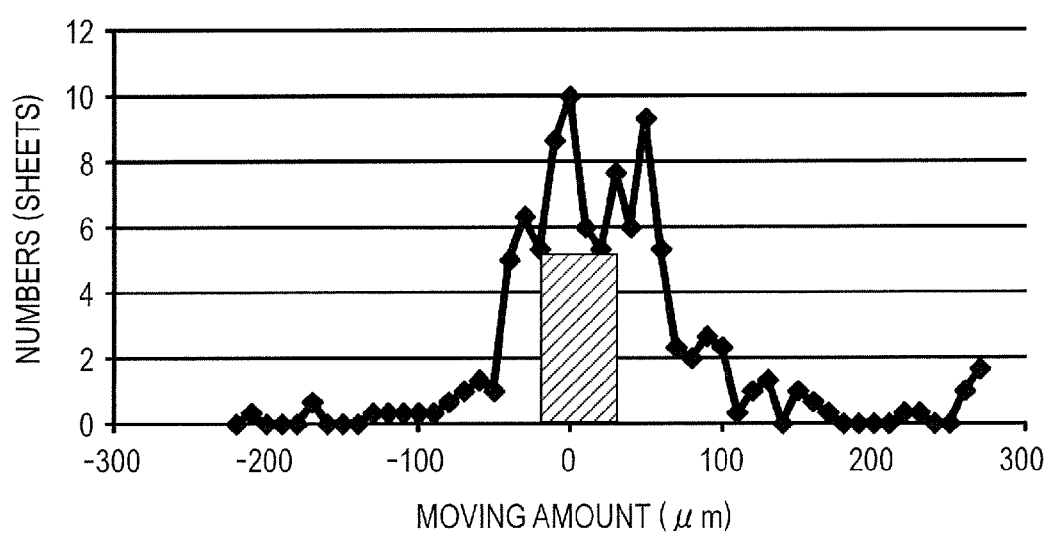
FIG. 8 is a histogram of the moving amount of the fundus in the second embodiment.

In the following, the process performed by the setting portion 511 will be described. FIG. 8 shows the computed moving amount of the eyeball. FIG. 8 is a histogram of the eye moving amount. Although the eyeball moves, it seldom moves by an amount (distance) larger than 100 µm, because the movement is limited by the internal fixation target. Since the tomographic images and the fundus images are captured simultaneously, the position information of each fundus image coincides with the relative position of scanning of the corresponding tomographic image. As with in the first embodiment, a high-quality composed image is formed by averaging the tomographic images.

A difference in the scanning position leads to a difference in the tomographic image. Averaging tomographic images at different scanning positions leads to blur of the composed image.

As with in the first embodiment, if a composed image is formed by averaging tomographic images captured by scanning substantially the same portion, speckles will appear in the composed image. In view of this, a limitation is placed on averaging of images of the same portion in synthesizing an image. In this embodiment, the images represented by the hatched portion in FIG. 8 are averaged to form a composed image as a new tomographic image. Specifically, to form a composed image from forty images, the images represented by the hatched portion (−25 µm to +35 µm) are averaged to form a high-quality image. More specifically, a composed image is formed by averaging five images with a moving amount not larger than ±5 µm from the reference position, five images with a moving amount in the range of −5 µm to −15 µm (inclusive of −5 µm, exclusive of −15 µm), five images with a moving amount in the range of +5 µm to +15 µm (inclusive of +5 µm, exclusive of +15 µm), five images with a moving amount in the range of −15 µm to −25 µm (inclusive of −15 µm, exclusive of −25 µm), five images with a moving amount in the range of +15 µm to +25 µm (inclusive of +15 µm, exclusive of +25 µm), and five images with a moving amount in the range of +25 µm to +35 µm (inclusive of +15 µm).

The apparatus may be adapted to display the number of images in each of the above ranges of moving amount together with the composed tomographic image to allow the operator to set the number of images in each of the ranges of moving amount.

As described above, position information is used with captured tomographic images to limit the number of tomographic images captured at positions close to each other to be averaged, and a composed image is formed using the limited number of images. By this process, a tomographic image having high image quality can be produced.

In this embodiment, because the beam diameter in the OCT is 20 μm, OTC scanned images with a moving amount in a range of 60 μm are used as tomographic images to be averaged. In cases where this method is applied to an apparatus equipped with a compensation optical system and having a small beam diameter (about 5 μm), it is preferred that the range of moving amount be set to about 15 μm.

To achieve both reduction of speckles and a high S/N ratio, it is more preferred to optimize the number of tomographic images to be averaged and the range of the degree of similarity (the range of the fundus scanning position) of the tomographic images to be averaged. Specifically, it is more preferred that the number of images to be averaged be approximately 100 and that the range be 2.5 times the OCT beam diameter.

<Others>

While a correlation function of images is used in calculating the degree of similarity in the first embodiment, the use of other calculation methods, e.g., segmenting a retina layer in images and calculating the degree of similarity using the data of the segmentation, will also be effective in achieving the same advantages.

While an SLO apparatus is used in the second embodiment to capture images of the fundus, the same advantages can be achieved with other apparatuses that can measure the movement of the eyeball, e.g., a fundus imaging apparatus (fundus camera) and an apparatus for imaging the anterior ocular segment (anterior camera).

Other Embodiments

The present invention can also be implemented by providing a system or apparatus with software (program) that carries out the functions of the above-described embodiment through a network or a storage medium of various forms and causing the computer (or CPU, MPU, or the like) of the system or apparatus to read and execute the program.

The present invention is not limited to the above-described embodiments, but various modifications and changes can be made to them without departing from the essence of the present invention. The above-described embodiments are directed to cases where the object to be measured is an eye. More specifically, the object to be inspected is an eye, a plurality of tomographic images are tomographic images of a portion including the macula retinae or optic papilla of the eye to be inspected, and similarity information is acquired by the similarity information acquiring unit on the basis of the curvature of the recessed portion of the macula retinae or optic papilla in each of the plurality of tomographic images. However, the present invention can also be applied to the measurement of other objects such as skin and body parts other than an eye. When applied to parts other than an eye, the apparatus according to the invention will be a medical apparatus other than an ophthalmic apparatus, e.g. an endoscope. Therefore, it is to be understood that the apparatus according to the present invention is an inspection apparatus exemplified by an ophthalmic apparatus and that the eye to be inspected is an example of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-051449, filed on Mar. 8, 2012, which is hereby incorporated by reference herein in its entirety.

What is claimed is:

1. An optical tomographic imaging apparatus comprising:
a scanning unit that scans a measuring light in an eye;
a control unit that controls the scanning unit to perform multiple scanning of the measuring light in what would be the same position of the eye if the eye were not to move;
a memory; and
a processor to perform operations comprising:
(a) acquiring, while the control unit controls the scanning unit to perform the multiple scanning, a plurality of tomographic images of the eye obtained by performing the multiple scanning of the measuring light, wherein each scanning of the multiple scanning is in a respective one of different positions of the eye corresponding to movements of the eye;
(b) performing alignment of the plurality of tomographic images in a scanning direction and a depth direction;
(c) determining, after performing the alignment, a respective plurality of degrees of similarity between one of the plurality of tomographic images and the other tomographic images of the plurality of tomographic images;
(d) selecting, from the plurality of tomographic images, tomographic images having different degrees of similarity in such a way that the number of tomographic images having degrees of similarity within a first range is larger than the number of tomographic images having degrees of similarity within a second range, the second range being lower than the first range; and
(e) forming a new tomographic image from the selected tomographic images.

2. An optical tomographic imaging apparatus according to claim 1, wherein the plurality of tomographic images are tomographic images of a portion including a macula retinae or optic papilla of the eye to be inspected, and
wherein the similarity information is acquired on the basis of a curvature of a recessed portion of the macula retinae or optic papilla in each of the plurality of tomographic images.

3. An optical tomographic imaging apparatus according to claim 1, wherein the degree of similarity is acquired on the basis of a moving amount of the eye to be inspected.

4. An optical tomographic imaging apparatus according to claim 3, wherein the moving amount of the eye to be inspected is obtained based on a fundus image of the eye obtained by scanning laser ophthalmoscope (SLO) scanning of the eye.

5. An optical tomographic imaging apparatus according to claim 4, wherein the moving amount of the eye to be inspected is obtained based on a change in position of a blood vessel between a first fundus image of the eye obtained by SLO scanning of the eye and a second fundus image of the eye obtained by SLO scanning of the eye.

6. An optical tomographic imaging apparatus according to claim 1, further comprising:
a display control unit that causes a display unit to display the new tomographic image.

7. An optical tomographic imaging apparatus according to claim 6, wherein the display control unit causes the display unit to display the plurality of tomographic images side by side and to display a display form showing the similarity information in association with each of the plurality of tomographic images.

8. An optical tomographic imaging apparatus according to claim 1, wherein the tomographic images of which the degree of similarities are equal to or larger than a predetermined value and different from others are selected.

9. An optical tomographic imaging apparatus according to claim 1, wherein each of the degrees of similarity is determined in accordance with a cross-correlation coefficient.

10. An optical tomographic imaging apparatus according to claim 1, wherein each of the degrees of similarity is determined in accordance with a sequential similarity detection algorithm.

11. An optical tomographic imaging apparatus according to claim 1, wherein the plurality of tomographic images comprise 100 images,
wherein the degrees of similarity comprise 99 degrees of similarity calculated by comparing a first image of the 100 images to each of the remaining 99 images of the 100 images,
wherein each of the degrees of similarity is measured as a percentage,
wherein the tomographic images are selected from each of (a) the first range, which is 98% to 100%, (b) the second range, which is 96% up to but not including 98%, and (c) a third range, which is 94% up to but not including 96%, selected in such a way that the number of tomographic images having relatively high degrees of similarity is larger than the number of tomographic images having relatively low degrees of similarity.

12. An optical tomographic imaging apparatus according to claim 11, wherein the selected tomographic images are selected such that moving amounts of the tomographic images are within a range that is less than or equal to 2.5 times a diameter of the measuring light scanned by the scanning unit.

13. An optical tomographic imaging apparatus according to claim 1, wherein the new tomographic image is formed using the selected tomographic images of the plurality of tomographic images without using any other tomographic images of the plurality of tomographic images.

14. An optical tomographic imaging apparatus according to claim 1, further comprising a display control unit that causes a display unit to display a count of how many tomographic images have a degree of similarity falling within the first range and a count of how many tomographic images have a degree of similarity falling within the second range.

15. An optical tomographic imaging apparatus according to claim 1, further comprising a display control unit that causes display, to an operator, of how many tomographic images have a degree of similarity falling within the first range and how many tomographic images have a degree of similarity falling within the second range, to allow the operator to control the number of tomographic images corresponding to each of the first range and the second range that are selected.

16. An optical tomographic imaging apparatus according to claim 1, wherein the selecting (1) selects (a) a tomographic image having a degree of similarity falling within the first range and (b) a tomographic image having a degree of similarity falling within the second range, and (2) does not select tomographic images having degrees of similarity falling within a third range different from the first range and the second range.

17. An optical tomographic imaging apparatus according to claim 16, further comprising a display control unit that causes a display unit to display a count of how many tomographic images have a degree of similarity falling within the first range and a count of how many tomographic images have a degree of similarity falling within the second range.

18. An optical tomographic imaging apparatus according to claim 1, wherein the selecting (1) selects (a) a plurality of tomographic images from tomographic images having degrees of similarity falling within the first range and (b) a plurality of tomographic images from tomographic images having degrees of similarity falling within the second range of degrees of similarity, and (2) does not select tomographic images from tomographic images having degrees of similarity falling within a third range different from the first range and the second range.

19. An optical tomographic imaging apparatus according to claim 1, wherein the apparatus further acquires, corresponding to the plurality of tomographic images of the eye, a respective plurality of fundus images of the eye obtained by scanning laser ophthalmoscope (SLO) scanning the eye.

20. An optical tomographic imaging apparatus according to claim 1, wherein tomographic images having degrees of similarity within a third range which is lower than the second range are selected in such a way that the number of tomographic images having degrees of similarity within the second range is larger than the number of tomographic images having degrees of similarity within the third range.

21. An optical tomographic imaging method comprising the steps of:
controlling a scanning unit to perform multiple scanning of a measuring light in what would be the same position of an eye if the eye were not to move;
acquiring, while controlling the scanning unit to perform the multiple scanning, a plurality of tomographic images of the eye obtained by performing the multiple scanning of the measuring light, wherein each scanning of the multiple scanning is in a respective one of different positions of the eye corresponding to movements of the eye;
performing alignment of the plurality of tomographic images in a scanning direction and a depth direction;
determining, after performing the alignment, a respective plurality of degrees of similarity between one of the plurality of tomographic images and the other tomographic images;
selecting, from the plurality of tomographic images, tomographic images having different degrees of similarity in such a way that the number of tomographic images having degrees of similarity within a first range is larger than the number of tomographic images having degrees of similarity within a second range, the second range being lower than the first range; and
forming a new tomographic image from the selected tomographic images.

22. An optical tomographic imaging method according to claim 21, wherein the plurality of tomographic images are tomographic images of a portion including a macula retinae or optic papilla of the eye to be inspected, and
wherein the similarity information acquired in the acquiring step is the similarity information on the basis of a curvature of a recessed portion of the macula retinae or optic papilla in each of the plurality of tomographic images.

23. An optical tomographic imaging method according to claim 21, wherein the similarity information acquired in the acquiring step is the degree of similarity on the basis of a moving amount of the eye to be inspected.

24. An optical tomographic imaging method according to claim 21, further comprising the step of:
   causing a display unit to display the new tomographic image.

25. An optical tomographic imaging method according to claim 24, wherein the display control unit causes the display unit to display the plurality of tomographic images side by side and to display a display form showing the similarity information in association with each of the plurality of tomographic images.

26. A non-transitory tangible medium having recorded thereon a program for causing a computer to execute the steps of the optical tomographic imaging method according to claim 21.

27. An optical tomographic imaging method according to claim 21, wherein in the selecting step, tomographic images of which the degree of similarities are equal to or larger than a predetermined value and different from others are selected.

28. An optical tomographic imaging method according to claim 21, wherein the new tomographic image is formed using the selected tomographic images of the plurality of tomographic images without using any other tomographic images of the plurality of tomographic images.

29. A non-transitory tangible medium having recorded thereon a program for causing a computer to execute the steps of the optical tomographic imaging method according to claim 28.

30. An optical tomographic imaging method according to claim 21, wherein tomographic images having degrees of similarity within a third range which is lower than the second range are selected in such a way that the number of tomographic images having degrees of similarity within the second range is larger than the number of tomographic images having degrees of similarity within the third range.

* * * * *